United States Patent [19]
Yaver et al.

[11] Patent Number: 5,939,305
[45] Date of Patent: Aug. 17, 1999

[54] GENE ENCODING CARBOXYPEPTIDASE OF *ASPERGILLUS NIGER*

[75] Inventors: Debbie Sue Yaver; Sheryl Ann Thompson, both of Davis, Calif.

[73] Assignee: Novo Nordisk Biotech Inc, Davis, Calif.

[21] Appl. No.: 08/967,149

[22] Filed: Nov. 10, 1997

Related U.S. Application Data

[62] Division of application No. 08/608,452, Feb. 28, 1996, Pat. No. 5,693,510, which is a division of application No. 08/309,341, Sep. 20, 1994, Pat. No. 5,594,119.

[51] Int. Cl.$^6$ .............................. C12N 9/62; C12N 1/20; C12Q 1/68; C07H 21/04
[52] U.S. Cl. .......................... 435/225; 435/6; 435/252.3; 435/254.11; 435/320.1; 536/23.2; 536/24.3
[58] Field of Search .................................. 435/225, 320.1, 435/6, 252.3, 254.11, 325; 536/23.2, 24.3

[56] References Cited

FOREIGN PATENT DOCUMENTS

WO 92/17595  10/1992  WIPO .

OTHER PUBLICATIONS

Dal Degan et al., 1992, Appl. Environ. Microbiol. 58(7) : 2144–2152.
Klionsky et al. (1990) Microbiological Reviews 54(3): 266–292.
Sørensen et al., Carlsberg Res. Commun., vol. 54, pp. 193–202 (1989).
Jarai et al., Gene, vol. 145, pp. 171–178 (1994).
Frederick et al., Gene, vol. 125, pp. 57–64 (1993).
Svendsen et al., FEBS Letters, vol. 333, No. 1,2, pp. 39–43 (1993).
Woolford et al., Molecular & Cellular Biology, vol. 6, No. 7, pp. 2500–2510 (1986).
Mukhtar et al. , Gene, vol. 121, pp. 173–177 (1992).
Ammerer et al., Molecular & Cellular Biology, vol. 6, No. 7, pp. 2490–2499 (1996).
Stevens et al., J. of Cell Biology, vol. 102, pp. 1551–1557 (1986).
Rodney Rothstein, Methods in Enzymology, vol. 194, pp. 281–301 (1991).
L. Valls et al., Cell, vol. 48, pp. 887–897 (1987).
Berka et al., Gene, vol. 86, No. 2, pp. 153–162 (1990).
Yaver et al., 34th Annual Meeting of ASCB, Molecular Biol. Cell, 5 (Suppl.) ISSN: 1059–1525 (1994).

*Primary Examiner*—Lisa Hobbs
*Attorney, Agent, or Firm*—Steve T. Zelson; Elias J Lambiris; Robert L. Starnes

[57] ABSTRACT

The present invention relates to a gene encoding an ascomycete or deuteromycete carboxypeptidase Y gene, and host cells modified so as to produce reduced amounts of carboxypeptidase.

10 Claims, 13 Drawing Sheets

FIG. 1A

```
         10         20         30         40         50         60
TCCTCTGCCT ACTCATCCCA TCACCATCTC AATTCATACC GCCCCCGTGG GGTTTCAGCA CCA 69         78         87         96        105        114
> |          |          |          |          |          |
  ATG AGA GTC CTT CCA GCT GCT ATG CTG GTT GGA GCG GCC ACG GCG GCC GTT CCT
  MET Arg Val Leu Pro Ala Ala MET Leu Val Gly Ala Ala Thr Ala Ala Val Pro 123        132        141        150        159        168
  |          |          |          |          |          |
  CCC TTC CAG CAG GTC CTT GGA GGT AAC GGT GCC AAG CAC GGT GCC GAC CAT GCG
  Pro Phe Gln Gln Val Leu Gly Gly Asn Gly Ala Lys His Gly Ala Asp His Ala 177        186        195        204        213        222
  |          |          |          |          |          |
  GCC GAG GTC CCT GCG GAT CAC AGT GCC GAC GGG TTC TCC AAG CCG CTG CAC GCA
  Ala Glu Val Pro Ala Asp His Ser Ala Asp Gly Phe Ser Lys Pro Leu His Ala 231        240        249        258        267        276
  |          |          |          |          |          |
  TTC CAG GAG GAG CTG AAG TCT CTC TTC GAC GAG GCT CGT AAG CTT TGG GAT GAG
  Phe Gln Glu Glu Leu Lys Ser Leu Phe Asp Glu Ala Arg Lys Leu Trp Asp Glu 285        294        303        312        321        330
  |          |          |          |          |          |
  GTG GCC AGC TTC TTC CCG GAG AGC ATG GAT CAG AAC CCT CTC TTT TCC CTC CCC
  Val Ala Ser Phe Phe Pro Glu Ser MET Asp Gln Asn Pro Leu Phe Ser Leu Pro
```

FIG. 1B

```
     339           348           357           366           375           384
      |             |             |             |             |             |
AAG   AAC   CGT   CCC   GAC   TCG   CAC   GAC   CAC   ATC   GTC   CGC   GGC   TCC
Lys   Asn   Arg   Pro   Asp   Ser   His   Asp   His   Ile   Val   Arg   Gly   Ser 393           402           411           420           429           438
      |             |             |             |             |             |
GAC   GTT   CAG   AGC   GTC   TGG   GTC   ACT   GGT   GAG   AAC   GGT   GAG   AAG   GAG   CGC   GAG   GTC
Asp   Val   Gln   Ser   Val   Trp   Val   Thr   Gly   Glu   Asn   Gly   Glu   Lys   Glu   Arg   Glu   Val 447           456           465           474           483           492
      |             |             |             |             |             |
GAT   GGC   AAG   CTG   GAA   GCC   TAT   GAT   CTC   AGG   GTC   AAG   AAG   ACC   GAT   CCT   GGC   TCT
Asp   Gly   Lys   Leu   Glu   Ala   Tyr   Asp   Leu   Arg   Val   Lys   Lys   Thr   Asp   Pro   Gly   Ser 501           510           519           528           537           546
      |             |             |             |             |             |
CTT   GGC   ATC   GAC   CCC   GGC   GTG   AAG   CAG   TAC   ACC   GGT   TAT   CTC   GAT   GAC   AAC   GAG
Leu   Gly   Ile   Asp   Pro   Gly   Val   Lys   Gln   Tyr   Thr   Gly   Tyr   Leu   Asp   Asp   Asn   Glu 555           564                               581                   601           611
      |             |                                 |                     |             |
AAT   GAT   AAG   CAT   TTG   TTC   TAC   T         GTAAGCACAC   CTTGGTTCAA   GATCACGCTT   TTTATATGCT
Asn   Asp   Lys   His   Leu   Phe   Tyr   Trp 621           631           641           650           659           668
 |             |             |             |             |             |
CTGGATATCT   AACGCAACTT   AG   GG   TTC   GAG   TCT   CGC   AAT   GAC   CCC   GAG   AAT   GAT
                                Phe   Glu   Ser   Arg   Asn   Asp   Pro   Glu   Asn   Asp
```

FIG. 1C

```
         677        686        695        704        713        722
         |          |          |          |          |          |
CCC GTT CTG TGG CTG AAC GGT CCT GGG TGC TCT TCC CTC ACC GGT CTC
Pro Val Leu Trp Leu Asn Gly Pro Gly Cys Ser Ser Leu Thr Gly Leu 731        740        749        758        767        776
         |          |          |          |          |          |
TTC ATG GAG CTT GGC CCT AGC AGC ATC AAC AAG ATC CAG CCG GTC TAC AAT
Phe MET Glu Leu Gly Pro Ser Ser Ile Asn Lys Ile Gln Pro Val Tyr Asn 785        794        803        812        821        830
         |          |          |          |          |          |
GAC TAC GCT TGG AAC TCC AAC GCG TCC GTG ATC TTC CTT GAC CAG CCT GTC AAT
Asp Tyr Ala Trp Asn Ser Asn Ala Ser Val Ile Phe Leu Asp Gln Pro Val Asn 839        848        857        866        875        884
         |          |          |          |          |          |
GTC GGT TAC TCC TAC AGT AAC TCT GCT GTC AGC GAC ACG GTC GCT GCT GGC AAG
Val Gly Tyr Ser Tyr Ser Asn Ser Ala Val Ser Asp Thr Val Ala Ala Gly Lys 893        902        911        920        929        938
         |          |          |          |          |          |
GAC GTC TAT GCC TTG CTT ACC CTC TTC AAA CAA TTC CCC GAG TAT GCT AAG
Asp Val Tyr Ala Leu Leu Thr Leu Phe Lys Gln Phe Pro Glu Tyr Ala Lys 947        956        965        974        983        992
         |          |          |          |          |          |
CAG GAC TTC CAC ATT GCC GGT GAA TCT TAT GCT GGT CAC TAT ATC CCC GTC TTC
Gln Asp Phe His Ile Ala Gly Glu Ser Tyr Ala Gly His Tyr Ile Pro Val Phe
```

FIG. 1D

```
1001                1010          1019          1028          1037          1046
 GCT TCG GAG ATC CTG TCT CAC AAG CGC AAC ATC AAC CTG CAG TCC GTT CTC
 Ala Ser Glu Ile Leu Ser His Lys Arg Asn Ile Asn Leu Gln Ser Val Leu 1055          1064          1073          1082          1091          1100
 ATT GGC AAC GGT CTC ACC GAC GGA TAC ACC GAG TAC CAG TAC CGT CCC ATG
 Ile Gly Asn Gly Leu Thr Asp Gly Tyr Thr Glu Tyr Gln Tyr Arg Pro MET 1109          1118          1127          1136          1145          1154
 GCC TGC GGT GAC GGC GGT TAC CCA GCT GTC TTG GAC GAG AGC TCC TGC CAG TCC
 Ala Cys Gly Asp Gly Gly Tyr Pro Ala Val Leu Asp Glu Ser Ser Cys Gln Ser 1163          1172          1181          1190          1199          1208
 ATG GAC AAC GCT CTT CCT CGC TGC CAG TCT ATG ATT GAG TCT TGC TAC AGT TCC
 MET Asp Asn Ala Leu Pro Arg Cys Gln Ser MET Ile Glu Ser Cys Tyr Ser Ser 1217          1226          1235          1244          1253          1262
 GAG AGC GCT TGG GTT TGT GTC CCG GCC TCC ATC TAC TGT AAC AAC GCC CTC CTT
 Glu Ser Ala Trp Val Cys Val Pro Ala Ser Ile Tyr Cys Asn Asn Ala Leu Leu 1271          1280          1289          1298          1307          1316
 GCC CCT TAC CAG CGC ACT GGG CAG AAC GTC TAT GAT GTC CGT GGT AAG TGC GAG
 Ala Pro Tyr Gln Arg Thr Gly Gln Asn Val Tyr Asp Val Arg Gly Lys Cys Glu
```

FIG. 1E

```
      1325         1334         1343         1352         1361         1370
        |            |            |            |            |            |
GAT AGC TCT AAC CTT TGC TAC TCG GCT ATG GGC TAC GTC AGC GAC TAC CTG AAC
Asp Ser Ser Asn Leu Cys Tyr Ser Ala MET Gly Tyr Val Ser Asp Tyr Leu Asn 1379         1388         1397         1406         1415         1424
        |            |            |            |            |            |
AAG CCC GAA GTC ATC GAG GCT GTT GGC GCT GAG GTC AAC GGC TAC GAC TCG TGC
Lys Pro Glu Val Ile Glu Ala Val Gly Ala Glu Val Asn Gly Tyr Asp Ser Cys 1433         1442         1451         1460         1469         1478
        |            |            |            |            |            |
AAC TTT GAC ATC AAC CGC AAC TTC CTC TTC CAC GGT GAC TGG ATG AAG CCC TAC
Asn Phe Asp Ile Asn Arg Asn Phe Leu Phe His Gly Asp Trp MET Lys Pro Tyr 1487         1496         1505         1514         1523         1532
        |            |            |            |            |            |
CAC CGC CTC GTT CCG GGA CTC CTG GAG CAG ATC CCT GTC TTG ATC TAT GCC GGT
His Arg Leu Val Pro Gly Leu Leu Glu Gln Ile Pro Val Leu Ile Tyr Ala Gly 1541         1550         1559         1568         1577         1586
        |            |            |            |            |            |
GAT GCT GAT TTC ATT TGC AAC TGG CTG GGC AAC AAG GCC TGG ACT GAA GCC CTG
Asp Ala Asp Phe Ile Cys Asn Trp Leu Gly Asn Lys Ala Trp Thr Glu Ala Leu 1595         1604         1613         1622         1631         1640
        |            |            |            |            |            |
GAG TGG CCC GGA CAG GCT GAA TAT GCC TCC GCT GAG CTG GAG GAT CTG GTC ATT
Glu Trp Pro Gly Gln Ala Glu Tyr Ala Ser Ala Glu Leu Glu Asp Leu Val Ile
```

FIG. 1F

```
     1649             1658             1667             1676             1685             1694
GTC  GAC  AAT  GAG  CAC  ACG  GGC  AAG  AAG  ATT  GGC  CAG  GTT  AAG  TCC  CAT  GGC  AAC
Val  Asp  Asn  Glu  His  Thr  Gly  Lys  Lys  Ile  Gly  Gln  Val  Lys  Ser  His  Gly  Asn 1703             1712             1721             1730             1739             1748
TTC  ACC  TTC  ATG  CGT  CTC  TAT  GGT  GGT  GGC  CAC  ATG  GTC  CCG  ATG  GAC  CAG  CCC
Phe  Thr  Phe  MET  Arg  Leu  Tyr  Gly  Gly  Gly  His  MET  Val  Pro  MET  Asp  Gln  Pro 1757             1766             1775             1784             1793             1809
                                                                                    ˅
GAG  TCG  AGT  CTC  GAG  TTC  TTC  AAC  CGC  TGG  TTG  GGA  GGT  GAA  TGG  TTC  TAA AGACGTGCTA
Glu  Ser  Ser  Leu  Glu  Phe  Phe  Asn  Arg  Trp  Leu  Gly  Gly  Glu  Trp  Phe 1819             1829             1839             1849             1859             1879
CCACCGCATA  TAGACTTTCT  GGTCATTTCG  GTGACACTGC  AGATATGTTT  CTTAACGATA  GTTTGAGCAT 1889             1899             1909             1919             1929             1949
GCTTGTCAAT  GCCCACTAGT  CCCGATCCTT  ATATGTTGCA  TGGTATCTAT  GAGTTTGTC  ACTATAGTGC 1959             1969             1979             1989             1999             2019
ATTATACATG  TGTACTTCGT  ATGAGAATGA  ATCGATCGCA  TTTACACGCA  TATAAATAGT  ACCCACCTCC 2029             2039             2049             2059             2068
GCCTGGACAT  GAATTAGGCC  CGGCCAGTCG  TTTACATACA  GTGCTAGAA
```

FIG. 2A

```
         10         20         30         40         50         60         70
GCGGCCGCTG CTACTTGCTT TTTCTAATTT GATACTTTTG TGTCCGTACC GTACCTTCCA GACCGCAAGG 80         90        100        110        120        130    139
TACCCATCCT CTACCTACTC ATCCCATCAT CATCTCGATT TCATACCAAC CCCGTTGGGT TTCAACACA start of propeptide
                                                              1 ↓  193
     148        157        166        175                         247
  ATG AGA GTT CTT CCA GCT ATG CTG GTT GGA GCG GGC ACT GCG GCC GTC CCT
  MET Arg Val Leu Pro Ala MET Leu Val Gly Ala Gly Thr Ala Ala Val Pro 202        211        220        229        238                301
  CCC TTC CAG CAG GTC CTT GGA GGT AAC GGT GCC AAG CAC GAC CAT GCG
  Pro Phe Gln Gln Val Leu Gly Gly Asn Gly Ala Lys His Asp His Ala 256        265        274        283        292                355
  GCC GAG GTC CCT GCG GAT CAC AGT GCC GAC GGG TTC TCC AAG CCG CTG CAC GCA
  Ala Glu Val Pro Ala Asp His Ser Ala Asp Gly Phe Ser Lys Pro Leu His Ala 310        319        328        337        346
  TTC CAG GAG GAG CTG AAG TCT CTC GAT GAG GCT CGT AAG CTC TGG GAT GAG
  Phe Gln Glu Glu Leu Lys Ser Leu Asp Glu Ala Arg Lys Leu Trp Asp Glu
```

FIG.2B

```
     364           373           382           391           400           409
     |             |             |             |             |             |
     GTT GCT AGC   TTC TTC CCG   GAG AGC ATG   GAT CAG AAC   CCT CTC TTC   TCC CTC CCC
     Val Ala Ser   Phe Phe Pro   Glu Ser MET   Asp Gln Asn   Pro Leu Phe   Ser Leu Pro 418                         436                         454                   463
     |                           |                           |                     |
     AAG AAC CGC   CGC CCC GAC   CAC CAC TGG   GAC CAC ATC   GTC CGC GGC   TCC
     Lys Asn Arg   Arg Pro Asp   His His Trp   Asp His Ile   Val Arg Gly   Ser 472                         490                                               517
     |                           |                                                 |
     GAC GTT CAG   AGC GTC TGG   GTT ACT GGT   GAG AAC GGT   GAG AAG GAG   GTC
     Asp Val Gln   Ser Val Trp   Val Thr Gly   Glu Asn Gly   Glu Lys Glu   Val
                                                             predicted N-terminus of mature CPY
     526                         544           553 ↓         562                   571
     |                           |             |             |                     |
     GAT GGC AAG   CTG GAA GCC   TAT GAT CTC   AGG GTC AAG   ACC GAT CCT   AGC TCT
     Asp Gly Lys   Leu Glu Ala   Tyr Asp Leu   Arg Val Lys   Thr Asp Pro   Ser Ser 580                         598           607                                 625
     |                           |             |                                   |
     GAC ATC GGC   GTA AAG CCT   CAG TAC ACC   GGT TAT CTC   GAT GAC AAC   GAG
     Asp Ile Gly   Val Lys Pro   Gln Tyr Thr   Gly Tyr Leu   Asp Asp Asn   Glu CTT GGC GAC   CCT GGC GTA   AAG CCT CAG   TAC ACC GGT   TAT CTC GAT   GAC AAC GAG
     Leu Gly Asp   Pro Gly Val   Lys Pro Gln   Tyr Thr Gly   Tyr Leu Asp   Asp Asn Glu
```

FIG. 2C

```
      634         643         652         661         670         679
AAC GAC AAG CAT CTG TTC TAC TGG TTC TTC GAG TCT CGC AAT GAC CCC GAG AAT
Asn Asp Lys His Leu Phe Tyr Trp Phe Phe Glu Ser Arg Asn Asp Pro Glu Asn 688         697         706         715         724         733
GAC CCT GTT GTT CTG TGG CTG AAC CTG GGT GGC CCT GGA TCC TCC CTC ACC GGT
Asp Pro Val Val Leu Trp Leu Asn Leu Gly Gly Pro Gly Ser Ser Leu Thr Gly 742         751         760         769         778         787
CTT TTC ATG GAG CTC GGC CCT AGC AGC ATC AAC AAG ATC CAG CCG GTC TAC
Leu Phe MET Glu Leu Gly Pro Ser Ser Ile Asn Lys Ile Gln Pro Val Tyr 796         805         814         823         832         841
AAC GAC TAC GCT TGG AAC TCC AAC GCG TCC GTG ATC TTC CTT GAC CAG CCT GTC
Asn Asp Tyr Ala Trp Asn Ser Asn Ala Ser Val Ile Phe Leu Asp Gln Pro Val 850         859         868         877         886         895
AAC GTC GGT TAC TCT TAC AGC AAC TCT GCT GTC AGC GAC ACC GTT CAG CCT GGC
Asn Val Gly Tyr Ser Tyr Ser Asn Ser Ala Val Ser Asp Thr Val Ala Gly 904         913         922         931         940         949
AAG GAC GTC TAT GCC TTG CTT ACC CTC TTC TTC AAA CAA TTC CCC GAG TAT GCC
Lys Asp Val Tyr Ala Leu Leu Thr Leu Phe Phe Lys Gln Phe Pro Glu Tyr Ala
```

FIG. 2D

```
      958         967         976         985         994        1003
AAG   CAG   GAC   TTC   CAC   ATT   GCC   GGT   GAA   TCC   TAT   ATC   GGT   CAC   TAT   ATC   CCC   GTC
Lys   Gln   Asp   Phe   His   Ile   Ala   Gly   Glu   Ser   Tyr   Ala   Gly   His   Tyr   Ile   Pro   Val 1012        1021        1030        1039        1048        1057
TTT   GCT   TCG   GAG   ATT   TTG   TCT   CAC   AAG   AAG   CGC   AAC   ATC   AAC   CTG   CAG   TCC   GTT
Phe   Ala   Ser   Glu   Ile   Leu   Ser   His   Lys   Lys   Arg   Asn   Ile   Asn   Leu   Gln   Ser   Val 1066        1075        1084        1093        1102        1111
CTT   ATT   GGC   AAC   GGT   CTC   ACC   GAC   GGT   CTC   ACT   CAG   TAC   GAG   TAC   TAC   CGT   CCC
Leu   Ile   Gly   Asn   Gly   Leu   Thr   Asp   Gly   Leu   Thr   Gln   Tyr   Glu   Tyr   Tyr   Arg   Pro 1120        1129        1138        1147        1156        1165
ATG   GCC   TGT   GGT   GAC   GGT   GGT   TAC   CCA   GCT   GTC   TTG   GAC   GAG   GGC   TCC   TGC   CAG
MET   Ala   Cys   Gly   Asp   Gly   Gly   Tyr   Pro   Ala   Val   Leu   Asp   Glu   Gly   Ser   Cys   Gln 1174        1183        1192        1201        1210        1219
GCC   ATG   GAC   AAC   GCC   CTT   CCT   CGC   TGC   CAG   TCT   ATG   ATT   GAG   TCT   TGC   TAT   AGT
Ala   MET   Asp   Asn   Ala   Leu   Pro   Arg   Cys   Gln   Ser   MET   Ile   Glu   Ser   Cys   Tyr   Ser 1228        1237        1246        1255        1264        1273
GCC   GAG   AGC   GCT   TGG   GTT   TGT   GTC   CCG   GCC   TCC   ATC   TAC   TGT   AAC   AAC   GCC   CTC
Ala   Glu   Ser   Ala   Trp   Val   Cys   Val   Pro   Ala   Ser   Ile   Tyr   Cys   Asn   Asn   Ala   Leu
```

FIG. 2E

```
     1282      1291      1300      1309      1318      1327
CTT  GCC  CCT  TAC  CAG  CGC  ACC  GGA  CAG  AAC  GTC  TAC  GAT  GTT  CGT  GGT  AAG  TGC
Leu  Ala  Pro  Tyr  Gln  Arg  Thr  Gly  Gln  Asn  Val  Tyr  Asp  Val  Arg  Gly  Lys  Cys 1336      1345      1354      1363      1372      1381
GAG  GAT  AGC  TCC  AAC  CTC  TGC  TAC  TCG  GCC  ATG  GGC  TAC  GTC  AGC  GAC  TAC  CTG
Glu  Asp  Ser  Ser  Asn  Leu  Cys  Tyr  Ser  Ala  MET  Gly  Tyr  Val  Ser  Asp  Tyr  Leu 1390      1399      1408      1417      1426      1435
AAC  AAG  GAG  GTC  ATT  GAG  GCT  GTT  GGC  GCT  GAG  GTC  AAC  GGC  TAC  GAC  TCG
Asn  Lys  Thr  Glu  Val  Ile  Glu  Val  Gly  Ala  Val  Gly  Ala  Glu  Val  Asn  Gly  Tyr  Asp  Ser 1444      1453      1462      1471      1480      1489
TGC  AAC  TTT  GAC  ATC  AAC  CGC  AAC  TTC  CTC  TTC  CAC  GGT  GAC  TGG  ATG  AAG  CCC
Cys  Asn  Phe  Asp  Ile  Asn  Arg  Asn  Phe  Leu  Phe  His  Gly  Asp  Trp  MET  Lys  Pro 1498      1507      1516      1525      1534      1543
TAC  CAC  CGT  CTC  GTT  CCG  GGA  CTC  CTG  GAG  CAG  ATC  CCT  GTC  CTG  ATC  TAC  GCT
Tyr  His  Arg  Leu  Val  Pro  Gly  Leu  Leu  Glu  Gln  Ile  Pro  Val  Leu  Ile  Tyr  Ala 1552      1561      1570      1579      1588      1597
TAC  CAC  GAT  TTC  ATC  TGC  AAC  TGG  CTG  GGC  AAC  AAG  GCC  TGG  ACT  GAA  GCC
Tyr  His  Asp  Phe  Ile  Cys  Asn  Trp  Leu  Gly  Asn  Lys  Ala  Trp  Thr  Glu  Ala

GGT  GAC  GCC  GAT  TTC  ATC  TGC  AAC  TGG  CTG  GGC  AAC  AAG  GCC  TGG  ACT  GAA  GCC
Gly  Asp  Ala  Asp  Phe  Ile  Cys  Asn  Trp  Leu  Gly  Asn  Lys  Ala  Trp  Thr  Glu  Ala
```

FIG. 2F

```
     1606       1615       1624       1633       1642       1651
CTT GAG TGG CCC GGA CAG GCT GAA TAT GCC TCC GCT AAG CTG GAG GAC CTG GTC
Leu Glu Trp Pro Gly Gln Ala Glu Tyr Ala Ser Ala Lys Leu Glu Asp Leu Val
     1660       1669       1678       1687       1696       1705
GTG GTC GAG AAT GAG CAC AAG AAG GGC AAG ATC GGC CAG GTC AAG TCC CAT GGC
Val Val Glu Asn Glu His Lys Lys Gly Lys Ile Gly Gln Val Lys Ser His Gly
     1714       1723       1732       1741       1750       1759
AAC TTC ACC TTC ATG CGT CTC TAT GGT GGC CAC ATG GTC CCG ATG GAC CAA
Asn Phe Thr Phe MET Arg Leu Tyr Gly Gly Gly His MET Val Pro MET Asp Gln
     1768       1777       1786       1795       1804       1813
CCC GAG TCG AGT CTT GAA TTC TTC AAC CGC TGG TTG GGA GGT GAA TGG TTT TAA
Pro Glu Ser Ser Leu Glu Phe Phe Asn Arg Trp Leu Gly Gly Glu Trp Phe
     1823       1833       1843       1853       1863       1873       1883
AGACGTGCTA TCACCGCATA TAGACTTTCC GGTCATTTCG GTGACACTGC AGATATGTTT CTTAACGATA
     1893       1903       1913       1923       1933       1943       1953
GTTTGAGGAT GCTTGTCAAT GCCCACTAAT CCCGAGCCTT ATGTTACATG GTATCTATGA GTTTGTCATT
     1963       1973       1983       1993       2002
ATAGTGCATT ATGCATTTGT ACTCCGTACG AGAATGAATC AGCGGCCGC
```

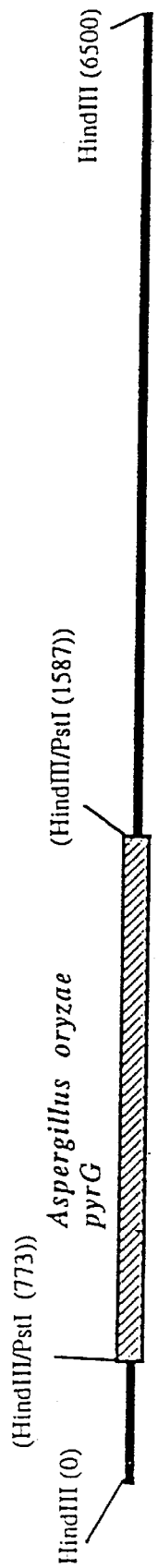

GENE ENCODING CARBOXYPEPTIDASE OF *ASPERGILLUS NIGER*

CROSS-REFERENCE TO RELATED APPLICATIONS

This application is a divisional application of application Ser. No. 08/608,452 filed on Feb. 28, 1996, now U.S. Pat. No. 5,693,510, which is a divisional of Ser. No. 08/309,341 filed on Sep. 20, 1994, now U.S. Pat. No. 5,594,119, the contents of which are fully incorporated herein by reference in their entirety.

FIELD OF THE INVENTION

The present invention relates to a gene encoding a fungal vacuolar protease. In particular, the invention relates to a carboxypeptidase gene of a filamentous ascomycete or deuteromycete fungus, such as those of the genus Aspergillus.

BACKGROUND OF THE INVENTION

The fungal vacuole is an acidic organelle that contains many hydrolases, including several proteases, and is essentially equivalent to the mammalian lysosome. Several of the hydrolases have been identified and characterized in one or more species of fungi, particularly in yeast; these include protease A(PEP4 or PrA), protease B(PrB), aminopeptidase (APE), dipeptidyl aminopeptidase B(DPAP B), carboxypeptidase Y(CPY), and carboxypeptidase S(CPS). Most of the vacuolar hydrolases are glycoproteins which are synthesized as inactive precursors. In fact, all the aforementioned proteases with the exception of APE have signal peptides that lead to transit through the secretory pathway. In the late golgi, vacuolar proteins are sorted from secretory proteins and eventually delivered to the vacuole. In addition to a signal peptide, most vacuolar proteins also have a propeptide which is cleaved upon delivery to the vacuole to generate the mature active enzyme. It has been demonstrated that the amino acid information in PrA and CPY required for vacuolar targeting is present within the propeptide(Johnson et al., Cell 48: 875–885, 1987; Rothman et al. PNAS USA 83: 3248–3252, 1989;

Valls et al., Cell 48: 887–897, 1989; Valls et al. J. Cell Biol. 111: 361–368, 1987). For CPY a string of four amino acid residues (QRPL) has been shown to be required for localization to the vacuole (Valls et al., J. Cell Biol. 111: 361–368, 1990). Once delivered to the vacuole, proteinase A (pep4)cleaves the propeptide of CPY and PrB leading to the activation of the proteases (Ammerer et al., Mol. Cell. Biol. 6: 2490–2499, 1986; Woolford et al., Mol. Cell. Biol. 6: 2500–2510, 1986).

In *S. cerevisiae*, three classes of mutants which mislocalize or missort vacuolar proteins have been identified (Bankaitis et al., PNAS USA 83: 9075–9079, 1986; Robinson et al., Mol. Cell. Biol., 8: 4936–4948, 1988; Rothman et al.,EMBO J. 8: 2057–2065, 1989; Rothman and Stevens, Cell 47: 1041–1051, 1986). These mutants are called vps or vacuolar protein sorting mutants. Several of these mutants are isolated using a selection based on the observation that overexpression of a vacuolar protease due to a high copy number on a plasmid leads to a secretion of vacuolar proteases (Stevens et al., J. Cell Biol. 102: 1551–1557, 1986; Rothman et al, PNAS USA 83: 3248–3242, 1986). This suggests that it is possible to saturate the sorting machinery within the late golgi.

In *S. cerevisiae*, it has also been demonstrated that strains deleted for PEP4, CPY and PrB produce higher levels of heterologous proteins due to a decrease in proteolysis of the desired product. Therefore, the vacuolar proteases in question are important from a commercial point of view because many of the fungi which produce them are used for recombinant production of heterologous proteins. The presence of these proteases in fermentation is undesirable, in that they can degrade the protein of interest, thereby significantly reducing yield. Elimination of the function of any given protease is facilitated by the disruption or deletion of the gene encoding it; however, doing so first requires identification and isolation of the corresponding gene in the host species of interest. As noted above, a few such genes have been isolated from various yeast strains; however, the genes encoding vacuolar proteases in the filamentous ascomycetes or deuteromycetes are less well known. For example, PEPC (Frederick et al., Gene 125: 57–64, 1993) and PEPE (Jarai et al., Gene 145: 171–178, 1994) genes coding for two other vacuolar proteases from *Aspergilus niger* have been isolated. PEPC codes for a proteinase B(PrB) homologue, and PEPE codes for a proteinase A homologue. The gene PEP4 from *Neurspora crassa* coding for a PrA homologue has also been cloned(Bowman, 17th Fungal Genetics Conference, 1993). For the first time herein is is described the gene encoding a vacuolar CPY from a filamentous ascomycete or deuteromycete.

SUMMARY OF THE INVENTION

The present invention relates to a nucleic acid construct comprising a sequence encoding a filamentous ascomycete or deuteromycete carboxypeptidase Y, as well as the recombinantly produced protein encoded thereby. As used herein, "nucleic acid construct" is intended to indicate any nucleic acid molecule of cDNA, genomic DNA, synthetic DNA or RNA origin. The term "construct" is intended to indicated a nucleic acid segment which may be single-or double-stranded, and which may be isolated in complete or partial form from a naturally occurring gene or which has been modified to contain segments of DNA which are combined and juxtaposed in a manner which would not otherwise exist in nature. The construct may optionally contain other nucleic acid segments. In a preferred embodiment, the sequence encodes a carboxypeptidase of the genus Aspergillus. The invention also provides a method for producing a non-carboxypeptidase-producing filamentous ascomycete or deuteromycete cell, which comprises disrupting or deleting the carboxypeptidase gene so as to prevent the expression of a functional enzyme, or treating the gene by classical mutagenesis using physical or chemical treatments to generate cells which are reduced or lacking in their ability to produce CPY. In addition, the invention also encompasses a filamentous ascomycete or deuteromycete which is unable to produce a functional carboxypeptidase enzyme, or which produces the carboxypeptidase in reduced amounts relative to the amount produced by the wild-type strain. Such organisms provide the basis for an improved method of recombinant protein production, wherein the carboxypeptidase-deficient microorganism is transformed with the nucleic acid construct encoding the protein of interest, and cultured under conditions conducive to the expression of the protein.

BRIEF DESCRIPTION OF THE FIGURES

FIGS. 1A–1F illustrates the DNA sequence and translation of the *A. niger* Bo-1 genomic CPY clone.

FIGS. 2A–2F illustrates the DNA sequence and translation of *A. niger* SFAG 2 CPY cDNA. The predicted site for signal peptidase cleavage and the N-terminus of mature CPY are indicated.

FIG. 3 illustrates the construct used in disruption CPY.

DETAILED DESCRIPTION OF THE INVENTION

Attempts to isolate an Aspergillus carboxypeptidase Y are initiated by designing a series of degenerate oligonucleotides, using the sequences of *S. cerevisiae* CPY, *Penicillium janthinellum* carboxypeptidase S1(Svedsen et al., FEBS 333: 39–43, 1993, and malt carboxypeptidase-MIII (Sørensen et al., Carlsberg Res. Commun. 54: 193–202, 1993). The oligonucleotide sequences are provided the examples below. These sequences are used as primers in various combinations in a PCR reaction using *Aspergillus niger* strain Bo-1 genomic DNA as a template. Two of the reactions(with primers 1-1 and 2-1 ; and 1-2 and 2-2 ) yield an 1100 bp amplification product, which is subcloned and sequenced, but none of the subclones has significant homology to CPY to be identified as the gene of interest.

Further PCR reactions with primers 3-1, 3-2, 4-1, 4-2, 2-1 and 2-2 are then made. In two of the reactions(primers 4-1 and 2-1; and 4-2 and 2-1) a 600 bp amplification product is obtained. This product is subcloned and 11 of the subclones sequenced; nine of these subclones are identical, and have homology to carboxypeptidaseY genes from other sources. The insert from one of the subclones is used to probe *A. niger* genomic DNA; hybridization with single bands is observed with BamHI. HindIII, and SalI digests, suggesting that a single CPY gene exists in *A. niger*. Hybridizations are done at 65° C. in 1.5× SSPE, 1.0% SDS, 0.5% non-fat milk and 200 µ/ml salmon sperm DNA.

An *A. niger* genomic DNA bank in EMBL4 is prepared and probed with the PCR CPY-derived gene fragment($^{32}$P-labeled), in order to isolate a full length gene. Out of approximately 28,000 plaques, 11 positives are picked; nine of these still hybridize with the probe after purification. A 5.5 HindIII fragment common to a majority of these clones is identified as the *A. niger* CPY gene. This fragment is subcloned and sequenced; the sequence of the fragment, including the CPY coding region and predicted amino acid sequence, is provided in FIG. 1.

Subsequently, a cDNA bank from a different *A. niger* strain is also screened. At least one full-length clone is identified from this library as well. This clone is sequenced and the sequence is depicted in FIG. 2. Both DNA sequences predict a CPY precursor of 557 amino acids in length. Based on a comparison with the homologous gene from *S. cerevisiae*, CPY from *A. niger* appears to have a prepropeptide of 137 or 138 amino acids. The gene contains one intron of 61 base pairs. A comparison of the. two *A. niger* sequences will show some difference in amino acid sequence, which presumably reflects the different strains from which the genomic and cDNA clones are isolated. A comparison with the amino acid sequences of the corresponding CPY genes of *S. cerevisiae* and *C. albicans* shows a 65% and 66% identity, respectively.

The present invention is not limited to the use of the sequences disclosed in FIGS. 1 and 2. First, the invention also encompasses nucleotide sequences which produce the same amino acid sequence as depicted in FIG. 1 or 2, but differ by virtue of the degeneracy of the genetic code. In addition, the difference in amino acid sequence shown for two strains of the same species shows that variation within the sequence of a single species is tolerated, and using the techniques described herein, such variants can readily be identified. Therefore, when "*A. niger*" is referred to in this context, it will be understood to encompass all such variations. In particular, the invention also encompasses any variant nucleotide sequence, and the protein encoded thereby, which protein retains at least about an 80%, preferably about 85%, and most preferably at least about 90–95% homology with the amino acid sequence depicted in FIG. 1 or 2, and which qualitatively retains the activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

In addition, the isolated gene provides a means for isolating homologous genes from other filamentous ascomycetes or deuteromycetes, such as other Aspergillus species, e.g., *A. oryzae, A. foetidus, A. japonicus, A. aculeatus*, or *A. nidulans*. Other non-Aspergillus filamentous ascomycete species include Fusarium species, such as *F. graminearum, F. oxysporum, F. solani, F. culmorum* (or corresponding teleomorphs) *Neurospora crassa, Trichoderma reesei, T. viridae, T. harzianum, T. longibranchiatum, Penicillium janthinellum, P, notatum, P. chrysogenum, P. camemberti, P. roqueforti, Humicola insolen, H. grisea* var. *thermoidea, H. lanuginosa, Scytalidium thermophilum, Myceliophthora thermophila*, and *Thielavia terrestris*. The gene, or an oligonucleotide based thereon, can be used as probes in southern hybridization to isolate homologous genes of these other species. In particular, such probes can be used under low to high stringency conditions(for example, prehybridization and hybridization at 42° C. in 5× SSPE, 0.3% SDS, 200 µg/ml sheared and denatured salmon sperm DNA, and either 50, 35 or 25% formamide for high, medium and low stringencies, respectively) for hybridization with the genomic or cDNA of the species of interest, following standard southern blotting procedures, in order to identify and isolate the corresponding CPY gene therein. A PCR reaction using the degenerate probes mentioned herein and genomic DNA or first-strand cDNA from a filamentous fungus may also yield a CPY-specific product which could then be used as a probe to clone the corresponding genomic or cDNA.

The present gene is particularly useful in the creation of carboxypeptidase-deficient mutants of filamentous ascomycetes such as Aspergillus. This can be achieved in a number of ways. In one method, as described in further detail below, a selectable marker is cloned into the middle of the CPY gene. The disrupted fragment is then released from the parental plasmid using restriction enzymes. The linearized DNA fragment is used to transform the chosen host cell. In the host cell, the homologous ends pair with the host cell chromosome, and the homologous recombination results in a chromosomal gene replacement. Useful selectable markers for use with fungal cell hosts include amdS, pyrG, argB, niaD, sC, and hygB. Alternately, a two-step process can be employed using a two-way selectable marker. In such a process, a plasmid containing a truncated CPY gene and the selectable marker gene is digested with a restriction enzyme which cuts once within the the CPY fragment in order to target integration to the CPY locus during transformation. The transformants are then grown on media which will select for the loss of the selectable marker gene, e.g., when the marker is pyrG, the medium may contain 5-fluorootic acid. The loss of the selectable gene usually occurs by a recombination between the wild type CPY and the introduced truncated CPY gene. Approximately 50% of the resulting strain should have only the truncated CPY gene while the other 50% will contain only the wild type gene. Such methods are described in Rothstein, Meth. Enzymol. 194, 281–301, 1991.

The CPY-deficient mutants so created are particularly useful in the expression of heterologous protein. By "heterologous protein" in the present context is meant a protein which is not native to the host cell, a native protein in which modifications have been made to alter the native sequence, or a native protein whose expression is quantitatively altered as a result of a manipulation of the host cell by recombinant DNA techniques. Also encompassed within this term are native proteins for which expression in the mutants involves the use of genetic elements not native to the host cell, or use of native elements which have been manipulated to function in a manner not normally seen in the host cell.

As already noted, the production of proteases by a chosen host cell can severely limit the yield of the desired protein by degrading the product before it can be recovered. The elimination or reduction in the amount of CPY produced by a host can therefore substantially increase the yield of any given protein, and can render an otherwise commercially unsuitable host cell commercially feasible for recombinant protein production. In a preferred embodiment, the CPY deficient cells produce at least 25% less, preferably at least 50% less, and most preferably at least 70% less CPY, up to total loss of CPY function, than the corresponding wild-type strain.

The mutant fungal cells of the present invention can be used in recombinant protein production in the same manner as the wild-type strains. Those skilled in the art will readily recognize routine variations from the specific embodiments described herein which are useful in adapting the methodology to the strains noted above. A gene of interest can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a gene to be used according to the invention is operably linked to the control sequences in the proper reading frame.

The expression vector may be any vector which may conveniently be subjected to recombinant DNA procedures, and the choice of vector will typically depend on the host cell into which it is to be introduced. In a preferred embodiment of the present invention, the host cell is a strain of the genus Aspergillus. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the sequence of the gene of interest should be operably connected to a suitable promoter sequence. The promoter may be any DNA sequence which shows transcriptional activity in the host cell of choice and may be derived from genes encoding proteins either homologous or heterologous to the host cell. For transcription in a fungal host, examples of useful promoters are those derived from the gene encoding *A. Oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. ozyzae* alkaline protease, *A. Oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the heterologous gene sequence. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. ozyzae*. Furthermore, selection may be accomplished by co-transformation, e.g. as described in WO 91/17243.

It is generally preferred that the expression gives rise to a product which is extracellular. The protein of interest may thus comprise a preregion permitting secretion of the expressed protein into the culture medium. If desirable, this preregion may be native to the protein of the invention or substituted with a different preregion or signal sequence, conveniently accomplished by substitution of the DNA sequences encoding the respective preregions. For example, the preregion may be derived from a glucoamylase or an amylase gene from an AspergilluS species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis subtilisin*. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The CPY-deficient mutants can be used to express any prokaryotic or eukaryotic protein of interest, and are preferably used to express eukaryotic proteins. Of particular interest for these cells is their use in expression of fungal enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, α-galactosidase, β-galactosidase, α-glucosidase, β-glucosidase, mannosidase, isomerase, invertase, transferase, ribonuclease, chitinase, and deoxyribonuclease. It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The mutants can also be used to express heterologous proteins of pharmaceutical interest such as hormones, growth factors, receptors, and the like.

The invention will be further illustrated by the following non-limiting examples.

EXAMPLES

I. ISOLATION OF THE *ASPERGILLUS NIGER* CPY GENE

A. MATERIALS AND METHODS i. Strains.

The following biological materials are used in the procedures described below. *Escherichia coli* K802(ek4- (nrca), mcrB, hsdR2, galK2, GalT22, supE44, metB1; *E. coli* SOLR(E14-(mcrA)Δ(mcrCB-hsdSMR-mr$^r$)171, sbcC, recB, recJ, uvrC, umuC::Tn5(kan$^r$), lac, gyrA96, relA1, thi-1, endA1, λR[F'proABlacI$^q$ZΔM15]Su$^-$, *E. coli* JM101supE, thi-1, Δ(lac-proAB), [F'traD36, proAB, lacI$^q$ZΔM15], *E. coli* XL-1 Blue recA1, endA1, gyrA96, thi-1, hsdR17, supE44, relA1, lac, [F'proAB, lacI$^q$ZΔM15, Tn10 (tet$^R$)], *Aspergillus niger* Bo-1, *A. niger* SFAG-2.

ii. PCR amplification.

PCR reactions are run using standard protocols with annealing steps done at 45° C. *A. niger* Bo-1 genomic DNA is used as template and the following degenerate oligonucleotides are used.
Primer 1-1(94-282)-GGIGGICCIGGITGYTC
Primer 1-2(94-283)-GGIGGICCIGGITGYAG
Primer 2-1(94-284)-CCIAGCCARTTRCADAT
Primer 2-2(94-285)-CCYAACCARTTRCADAT
Primer 3-1(94-331)-GTIGGITTYTCITAYTCIGG
Primer 3-2(94-332)-GTIGGITTYAGYTAYAGYGG
Primer 4-1(94-329)-GARTCITAYGCIGGICAYTA
Primer 2-1(94-284)-GARAGYTAYGCIGGICAYTA
In the above primers, I stands for inosine, Y for C or T, R for A or G, and D for A, G or T.

iii. Subcloning PCR products.

PCR products are subcloned for sequencing using the TA Cloning Kit(Invitrogen) following the manufacturer's protocols.

iv. In vivo excision from Lambda Zap II.

From the CPY cDNA Lambda Zap clones, a plasmid is rescued containing the cDNA inserts in a pBluescript SK-vector by passage through the *E. coli* strain SOLR following the protocols provided by Stratagene.

v. DNA sequencing.

Nucleotide sequencing is determined using TAQ polymerase cycle-sequencing with fluorescent labeled nucleotides. The sequencing reactions are electrophoresed on an Applied Biosystems automatic DNA sequencer(Model 363A, version 1.2.0). The following CPY specific primers are used, in addition to the M13 reverse(−48) and M13 (−20) forward primers(Sanger et al., J. Mol. Biol. 143: 163–178):

| | |
|---|---|
| 94-376 | TCGCTGCCAGTCTATGATTGA |
| 94-377 | ACATCAACCGCAACTTCCTCT |
| 94-378 | TTGCCAATGAGAACGGACTGC |
| 94-379 | CGCACTTACCACGGACATCAT |
| 94-503 | CAAGCATCCTCAAACTATCGT |
| 94-504 | GAGACGCATGAAGGTGAAGTT |
| 94-505 | GCCGTCCCTCCCTTCCAGCAG |
| 94-506 | GTGCCGACGGGTTCTCCAAGC |
| 94-507 | GCAGCGAGGAAGAGCGTTGTC |
| 94-510 | GGGTCATTCTCGGGGTCATTG |
| 94-511 | GACCCCGAGAATGACCCTGTT |
| 94-512 | GTAGGGCTTCATCCAGTCACC |
| 94-513 | TCTCACCGTTCTCACCAGTAA |
| 94-514 | TCCCTCCCAAGAAGCACAAC |
| 94-528 | AGCGTCTGGGTTACTGGTGAG |
| 94-529 | AAGATCGGCCAGGTCAAGTCC |
| 94-530 | GAGACGGTGGTAGGGCTTCAT |
| 94-531 | AACGTCGGTTACTCTTACAGC |
| 94-532 | GTGGTCGGGCGGCGGTTGTG |
| 94-533 | TGTTTGAAGAAGAGGGTAAGC |
| 94-575 | CGCTGCTACTTGATTTTTCTA |
| 94-576 | CTCAGCGCCAACAGCCTCAAT |
| 94-577 | ACCTGCAGTCCGTTCTTATTG |
| 94-634 | TGCGATCGATTCATTCTCATC |
| 94-635 | GGAGTAACCGACATTGACAGG |
| 94-636 | CCTGTCAATGTCGGTTACTCC |
| 94-637 | GTCCCATGGCAACTTCACCTT |
| 94-646 | CTTCTCACCGTTCTCACCAGT |
| 94-647 | CGAGACTCGAAGAACCCTAAG |

B. RESULTS

Using *A. niger* Bo-1 genomic DNA as template PCR reactions are done using various combinations of the CPY specific degenerate oligonucleotides, primers 1-1, 1-2, 2-1, and 2-2 (FIG. 1). All reactions are done using one cycle at 95° C. for 5 minutes, 45° C. for 1 minute and 72° C. for 2 minutes followed by 25 cycles at 95° C. for 1 minute, 45° C. for one minute and 72° C for 2 minutes. Aliquots(l0gl) of the reactions were electrophoresed on an agarose gel, and in two of the reactions, one with primers 1-2 and 2-1 and one with primers 1-2 and 2-2, an amplification product of approximately 1100 bp is the major species. The predicted size of a product using these oligonucleotide combinations assuming there are no introns within the gene is 900 bp. the 1100 bp amplification product is subcloned and sequenced using the forward and reverse primers. Seven of the subclones are sequenced; however, none of them by homology code for CPY.

PCR reactions using various combinations of primers 3-1, 3-2, 4-1, 4-2, 2-1 and 2-2 are run using the same conditions as above. Aliquots are electrophoresed on an agarose gel, and in two of the reactions, one with primers 4-1 and 2-1 and one with primers 4-2 and 2-1, an amplification product of approximately 600 bp is the major species. The expected size for this amplification product based on homology to other carboxypeptidases is 600 bp. The 600 bp amplification product is subcloned and the DNA sequence is determined for 11 of the subclones using the forward and reverse primers. Nine of the 11 subclones, based on identity of 69% to S. cerevisiae, code for CPY from A. niger . All 9 are identical to one another suggesting there is only one gene for carboxypeptidase in A. niger. The subclone containing the A. niger CPY PCR product of 600 bp is designated pDSY17.

A Southern blot of A. niger Bo-1 genomic DNA is probed with the insert from pDSY17. The probe is radiolabeled using a nick-translation kit from Gibco-BRL. Hybridization conditions used are 60° C. in 1.5× SSPE, 1% SDS, 0.5% nonfat milk and 200 µg/ml salmon sperm DNA. The blot is washed at 65° C. for 15 minutes twice in 0.2× SSC, 1% SDS and 0.1% Na pyrophosphate. In the BamHI, HindIII and SAlI digests, single bands of approximately 10, 5.5 and 7 kb, respectively hybridize to the CPY probe.

In order to isolate the full gene for CPY, a genomic bank in EMBL4 of A. niger Bo-1 containing approximately 26,000 recombinants is probed with the PCR-derived CPY gene fragment, radiolabeled with the Gibco-BRL nick translation kit. Approximately 28,000 plaques are lifted to filters and probed. Eleven positives from these plates are picked. After purification, 9 of the primary clones still hybridized with the CPY probe. DNA is isolated from the 9 clones, and restriction digests are done in order to begin characterizing them. From the restriction patterns, 7 of the 9 are identical. The other two clones are unique. From Southern digests of the clones, it is determined that 8 of the 9 have the same HindIII fragment of approximately 5.5 kb which hybridizes to the CPY probe. The clone which does not contain the same HindIII fragment contains a larger (>12 kb) HindIII fragment which hybridizes to the CPY probe. The common HindIII fragment is subcloned for DNA sequencing. The genomic DNA sequence and predicted amino acid sequence is shown in FIG. 1.

A cDNA bank in Lambda ZAPII(Stratagene) of A. niger SFAG-2 is also screened. Approximately 42,000 plaques are lifted to filter and probed with the CPY probe as above, and 112 of these plaques appear to hybridize under the stringent conditions defined above. Twenty of the initial positives are picked and rescreened, and upon purification, 18 still hybridize with the CPY probe. From 4 of the positive clones, DNA is isolated using the in vivo excision protocol provided with the Lambda Zap kit. The rescued plasmids are digested with EcoRI and electrophoresed on an agarose gel to determine the sizes of the inserts. Two of the clones(2-1 and 3-2) appear to have large enough inserts to contain the 20 full length cDNA for CPY, and each contains two EcoRI fragments of approximately 1700 and 250 bp. The predicted size for a full length cDNA is approximately 1600 bp. The other two cDNA clones (2-2 and 2-4) have smaller inserts; however, they all contain the 250 bp EcoRI fragment. Partial DNA sequences of clones 3-2 and 2-2 are determined, and 3-2 contains the full-length cDNA while clone 2-2 is truncated at the 5' end by about 200 bp.

The complete cDNA sequence is determined on both strands(FIG. 2). The cDNA is predicted to code for a CPY precursor of 557 amino acids in length. To date most of the nucleotide differences found between the cDNA and genomic clones are within the wobble which is not surprising since they come from two different A. niger strains. Based on an alignment with CPY from S. cerevisiae, CpY from A. niger appears to have both a signal peptide and a propeptide and the mature CPY protein is either 419 or 420 amino acids in length. A. niger CPY has approximately 65% and 66% identity to CPY from the yeasts S. cerevisiae and C. albicans (Mukhtar et al., Gene 121: 173-177, 1992), respectively.

II. PREPARATION OF A CPY-DEFICIENT MUTANT

In order to create an A. niger strain deleted for CPY, a construct in which the A. oryzae pyrG gene is inserted into the coding region of CPY is made(FIG. 3). An ~6.5 kb HindIII fragment containing almost the entire gene of CPY and ~6kb downstream of the gene is subcloned into a pKS+(Stratagene) derivative in which the PstI site has been destroyed. The resulting recombinant is digested with PstI to delete an 815 bp fragment from the CPY coding region, and the overhangs created by digestion with PstI are blunted by the addition of T4 DNA polymerase and all 4 dNTPs. The resulting blunt-end vector is ligated to an ~3.8 kb blunt-end fragment obtained by digestion with HindIII followed by a fill-reaction using Klenow fragment. The final construct in which the CPY gene has the pyrG inserted is digested with HindIII to create a linear fragment which is used to transform an A. niger pyrG strain selecting for growth on minimal medium plates. Transformants are screened by Southern blotting to determine which strains contain a disrupted CPY gene. The transformants are further analyzed by Western blotting to look for the absence of CPY intracellularly. Once a strain is identified as containing a disruption of CPY, the effect on heterologous protein is determined.

Deposit of Biological Materials

The following biological materials have been deposited on Sep. 13, 1994 in Agricultural Research Service Culture Collection (NRRL) 1815 North University Street, Peoria, Ill. 61604.

| Cell line | Accession No. |
|---|---|
| E. coli containing pDSY23 (EMCC #0120) | NRRL B-21326 |

What is claimed is:

1. An isolated Aspergillus niger carboxypeptidase Y.

2. An isolated carboxypedtidase Y encoded by a nucleic acid sequence which hybridizes with SEQ ID NO:1 under high stringency conditions.

3. The carboxypeptidase Y of claim 2 in which the nucleic acid sequence is obtained from Aspergillus, Fusarium, Penicillium, Humicola, Trichoderma, Scytalidium; Myceliophthora or Thielavia.

4. The carboxypeptidase Y of claim 3 in which the nucleic acid sequence is obtained from Aspergillus.

5. The carboxypeptidase Y of claim 2 which has an amino acid sequence of SEQ ID NO:2.

6. An isolated carboxypeptidase Y encoded by a nucleic acid sequence which hybridizes with SEQ ID NO:3 under high stringency conditions.

7. The carboxypeptidase y of claim 6 in which the nucleic acid sequence is obtained from Aspergillus, Fusarium, Penicillium, Humicola, Trichoderma, Scytalidium, Myceliophthora or Thielavia.

8. The carboxypeptidase Y claim 7 in which the nucleic acid sequence is obtained from Aspergillus.

9. The carboxypeptidase Y of claim 6 which has an amino acid sequence of SEQ ID NO:4.

10. The carboxypeptidase Y of claim 1, which is encoded by the nucleic acid sequence contained in pDSY23 contained in E. coli NRRLB-21326.

* * * * *

UNITED STATES PATENT AND TRADEMARK OFFICE
CERTIFICATE OF CORRECTION

PATENT NO. : 5,939,305
DATED : August 17, 1999
INVENTOR(S) : Yaver et al

It is certified that error appears in the above-identified patent and that said Letters Patent is hereby corrected as shown below:

Col. 26, Line 45: delete "y" and insert --Y--

Signed and Sealed this

Twenty-ninth Day of February, 2000

Attest:

Attesting Officer

Q. TODD DICKINSON

Commissioner of Patents and Trademarks

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 2068 base pairs
    (B) TYPE: nucleic acid
    (C) STRANDEDNESS: double
    (D) TOPOLOGY: linear (ii) MOLECULE TYPE: Genomic DNA (vi) ORIGINAL SOURCE:
    (A) ORGANISM: Aspergillus niger (ix) FEATURE:
    (A) NAME/KEY: intron
    (B) LOCATION: 572..632

(ix) FEATURE:
    (A) NAME/KEY: CDS
    (B) LOCATION: join (571..633)

(xi) SEQUENCE DESCRIPTION: SEQ ID NO: 1:

```
TCCTCTGCCT ACTCATCCCA TCACCATCTC AATTCATACC GCCCCCGTGG GGTTTCAGCA        60

CCA ATG AGA GTC CTT CCA GCT GCT ATG CTG GTT GGA GCG GCC ACG GCG        108
    Met Arg Val Leu Pro Ala Ala Met Leu Val Gly Ala Ala Thr Ala
    1               5                   10                  15

GCC GTT CCT CCC TTC CAG CAG GTC CTT GGA GGT AAC GGT GCC AAG CAC        156
Ala Val Pro Pro Phe Gln Gln Val Leu Gly Gly Asn Gly Ala Lys His
                20                  25                  30

GGT GCC GAC CAT GCG GCC GAG GTC CCT GCG GAT CAC AGT GCC GAC GGG        204
Gly Ala Asp His Ala Ala Glu Val Pro Ala Asp His Ser Ala Asp Gly
            35                  40                  45

TTC TCC AAG CCG CTG CAC GCA TTC CAG GAG GAG CTG AAG TCT CTC TCT        252
Phe Ser Lys Pro Leu His Ala Phe Gln Glu Glu Leu Lys Ser Leu Ser
        50                  55                  60

GAC GAG GCT CGT AAG CTT TGG GAT GAG GTG GCC AGC TTC TTC CCG GAG        300
Asp Glu Ala Arg Lys Leu Trp Asp Glu Val Ala Ser Phe Phe Pro Glu
65                  70                  75

AGC ATG GAT CAG AAC CCT CTC TTT TCC CTC CCC AAG AAG CAC AAC CGC        348
Ser Met Asp Gln Asn Pro Leu Phe Ser Leu Pro Lys Lys His Asn Arg
80                  85                  90                  95

CGT CCC GAC TCG CAC TGG GAC CAC ATC GTC CGC GGC TCC GAC GTT CAG        396
Arg Pro Asp Ser His Trp Asp His Ile Val Arg Gly Ser Asp Val Gln
                100                 105                 110

AGC GTC TGG GTC ACT GGT GAG AAC GGT GAG AAG GAG CGC GAG GTC GAT        444
Ser Val Trp Val Thr Gly Glu Asn Gly Glu Lys Glu Arg Glu Val Asp
            115                 120                 125

GGC AAG CTG GAA GCC TAT GAT CTC AGG GTC AAG AAG ACC GAT CCT GGC        492
Gly Lys Leu Glu Ala Tyr Asp Leu Arg Val Lys Lys Thr Asp Pro Gly
        130                 135                 140

TCT CTT GGC ATC GAC CCC GGC GTG AAG CAG TAC ACC GGT TAT CTC GAT        540
Ser Leu Gly Ile Asp Pro Gly Val Lys Gln Tyr Thr Gly Tyr Leu Asp
    145                 150                 155

GAC AAC GAG AAT GAT AAG CAT TTG TTC TAC GTAAGCACAC CTTGGTTCAA          590
Asp Asn Glu Asn Asp Lys His Leu Phe Tyr
160                 165

GATCACGCTT TTTATATGCT CTGGATATCT AACGCAACTT AG TGG TTC TTC GAG        644
                                               Trp Phe Phe Glu
                                               170
```

```
TCT CGC AAT GAC CCC GAG AAT GAT CCC GTT GTT CTG TGG CTG AAC GGT    692
Ser Arg Asn Asp Pro Glu Asn Asp Pro Val Val Leu Trp Leu Asn Gly
    175                 180                 185

GGC CCT GGG TGC TCT TCC CTC ACC GGT CTC TTC ATG GAG CTT GGC CCT    740
Gly Pro Gly Cys Ser Ser Leu Thr Gly Leu Phe Met Glu Leu Gly Pro
190                 195                 200                 205

AGC AGC ATC AAC AAG AAG ATC CAG CCG GTC TAC AAT GAC TAC GCT TGG    788
Ser Ser Ile Asn Lys Lys Ile Gln Pro Val Tyr Asn Asp Tyr Ala Trp
                210                 215                 220

AAC TCC AAC GCG TCC GTG ATC TTC CTT GAC CAG CCT GTC AAT GTC GGT    836
Asn Ser Asn Ala Ser Val Ile Phe Leu Asp Gln Pro Val Asn Val Gly
            225                 230                 235

TAC TCC TAC AGT AAC TCT GCT GTC AGC GAC ACG GTC GCT GCT GGC AAG    884
Tyr Ser Tyr Ser Asn Ser Ala Val Ser Asp Thr Val Ala Ala Gly Lys
        240                 245                 250

GAC GTC TAT GCC TTG CTT ACC CTC TTC TTC AAA CAA TTC CCC GAG TAT    932
Asp Val Tyr Ala Leu Leu Thr Leu Phe Phe Lys Gln Phe Pro Glu Tyr
    255                 260                 265

GCT AAG CAG GAC TTC CAC ATT GCC GGT GAA TCT TAT GCT GGT CAC TAT    980
Ala Lys Gln Asp Phe His Ile Ala Gly Glu Ser Tyr Ala Gly His Tyr
270                 275                 280                 285

ATC CCC GTC TTC GCT TCG GAG ATC CTG TCT CAC AAG AAG CGC AAC ATC   1028
Ile Pro Val Phe Ala Ser Glu Ile Leu Ser His Lys Lys Arg Asn Ile
                290                 295                 300

AAC CTG CAG TCC GTT CTC ATT GGC AAC GGT CTC ACC GAC GGA TAC ACC   1076
Asn Leu Gln Ser Val Leu Ile Gly Asn Gly Leu Thr Asp Gly Tyr Thr
            305                 310                 315

CAG TAC GAG TAC TAC CGT CCC ATG GCC TGC GGT GAC GGC GGT TAC CCA   1124
Gln Tyr Glu Tyr Tyr Arg Pro Met Ala Cys Gly Asp Gly Gly Tyr Pro
        320                 325                 330

GCT GTC TTG GAC GAG AGC TCC TGC CAG TCC ATG GAC AAC GCT CTT CCT   1172
Ala Val Leu Asp Glu Ser Ser Cys Gln Ser Met Asp Asn Ala Leu Pro
    335                 340                 345

CGC TGC CAG TCT ATG ATT GAG TCT TGC TAC AGT TCC GAG AGC GCT TGG   1220
Arg Cys Gln Ser Met Ile Glu Ser Cys Tyr Ser Ser Glu Ser Ala Trp
350                 355                 360                 365

GTT TGT GTC CCG GCC TCC ATC TAC TGT AAC AAC GCC CTC CTT GCC CCT   1268
Val Cys Val Pro Ala Ser Ile Tyr Cys Asn Asn Ala Leu Leu Ala Pro
                370                 375                 380

TAC CAG CGC ACT GGG CAG AAC GTC TAT GAT GTC CGT GGT AAG TGC GAG   1316
Tyr Gln Arg Thr Gly Gln Asn Val Tyr Asp Val Arg Gly Lys Cys Glu
            385                 390                 395

GAT AGC TCT AAC CTT TGC TAC TCG GCT ATG GGC TAC GTC AGC GAC TAC   1364
Asp Ser Ser Asn Leu Cys Tyr Ser Ala Met Gly Tyr Val Ser Asp Tyr
        400                 405                 410

CTG AAC AAG CCC GAA GTC ATC GAG GCT GTT GGC GCT GAG GTC AAC GGC   1412
Leu Asn Lys Pro Glu Val Ile Glu Ala Val Gly Ala Glu Val Asn Gly
    415                 420                 425

TAC GAC TCG TGC AAC TTT GAC ATC AAC CGC AAC TTC CTC TTC CAC GGT   1460
Tyr Asp Ser Cys Asn Phe Asp Ile Asn Arg Asn Phe Leu Phe His Gly
430                 435                 440                 445

GAC TGG ATG AAG CCC TAC CAC CGC CTC GTT CCG GGA CTC CTG GAG CAG   1508
Asp Trp Met Lys Pro Tyr His Arg Leu Val Pro Gly Leu Leu Glu Gln
                450                 455                 460

ATC CCT GTC TTG ATC TAT GCC GGT GAT GCT GAT TTC ATT TGC AAC TGG   1556
Ile Pro Val Leu Ile Tyr Ala Gly Asp Ala Asp Phe Ile Cys Asn Trp
            465                 470                 475

CTG GGC AAC AAG GCC TGG ACT GAA GCC CTG GAG TGG CCC GGA CAG GCT   1604
Leu Gly Asn Lys Ala Trp Thr Glu Ala Leu Glu Trp Pro Gly Gln Ala
        480                 485                 490
```

```
GAA TAT GCC TCC GCT GAG CTG GAG GAT CTG GTC ATT GTC GAC AAT GAG   1652
Glu Tyr Ala Ser Ala Glu Leu Glu Asp Leu Val Ile Val Asp Asn Glu
    495                 500                 505

CAC ACG GGC AAG AAG ATT GGC CAG GTT AAG TCC CAT GGC AAC TTC ACC   1700
His Thr Gly Lys Lys Ile Gly Gln Val Lys Ser His Gly Asn Phe Thr
510                 515                 520                 525

TTC ATG CGT CTC TAT GGT GGT GGC CAC ATG GTC CCG ATG GAC CAG CCC   1748
Phe Met Arg Leu Tyr Gly Gly Gly His Met Val Pro Met Asp Gln Pro
                    530                 535                 540

GAG TCG AGT CTC GAG TTC TTC AAC CGC TGG TTG GGA GGT GAA TGG TTC   1796
Glu Ser Ser Leu Glu Phe Phe Asn Arg Trp Leu Gly Gly Glu Trp Phe
            545                 550                 555

TAA AGACGTGCTA CCACCGCATA TAGACTTTCT GGTCATTTCG GTGACACTGC        1849

AGATATGTTT CTTAACGATA GTTTGAGCAT GCTTGTCAAT GCCCACTAGT CCCGATCCTT 1909

ATATGTTGCA TGGTATCTAT GAGTTTTGTC ACTATAGTGC ATTATACATG TGTACTTCGT 1969

ATGAGAATGA ATCGATCGCA TTTACACGCA TATAAATAGT ACCCACCTCC GCCTGGACAT 2029

GAATTAGGCC CGGCCAGTCG TTTACATACA GTGCTAGAA                        2068

(2) INFORMATION FOR SEQ ID NO: 2:

(i) SEQUENCE CHARACTERISTICS:
        (A) LENGTH: 557 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Aspergillus Niger (xi) SEQUENCE DESCRIPTION: SEQ ID NO: 2:

Met Arg Val Leu Pro Ala Ala Met Leu Val Gly Ala Ala Thr Ala Ala
1               5                   10                  15

Val Pro Pro Phe Gln Gln Val Leu Gly Gly Asn Gly Ala Lys His Gly
                20                  25                  30

Ala Asp His Ala Ala Glu Val Pro Ala Asp His Ser Ala Asp Gly Phe
            35                  40                  45

Ser Lys Pro Leu His Ala Phe Gln Glu Glu Leu Lys Ser Leu Ser Asp
    50                  55                  60

Glu Ala Arg Lys Leu Trp Asp Glu Val Ala Ser Phe Phe Pro Glu Ser
65                  70                  75                  80

Met Asp Gln Asn Pro Leu Phe Ser Leu Pro Lys Lys His Asn Arg Arg
                85                  90                  95

Pro Asp Ser His Trp Asp His Ile Val Arg Gly Ser Asp Val Gln Ser
                100                 105                 110

Val Trp Val Thr Gly Glu Asn Gly Glu Lys Glu Arg Glu Val Asp Gly
            115                 120                 125

Lys Leu Glu Ala Tyr Asp Leu Arg Val Lys Lys Thr Asp Pro Gly Ser
    130                 135                 140

Leu Gly Ile Asp Pro Gly Val Lys Gln Tyr Thr Gly Tyr Leu Asp Asp
145                 150                 155                 160

Asn Glu Asn Asp Lys His Leu Phe Tyr Trp Phe Phe Glu Ser Arg Asn
                165                 170                 175

Asp Pro Glu Asn Asp Pro Val Val Leu Trp Leu Asn Gly Gly Pro Gly
                180                 185                 190
```

```
Cys Ser Ser Leu Thr Gly Leu Phe Met Glu Leu Gly Pro Ser Ser Ile
        195                 200                 205

Asn Lys Lys Ile Gln Pro Val Tyr Asn Asp Tyr Ala Trp Asn Ser Asn
210                 215                 220

Ala Ser Val Ile Phe Leu Asp Gln Pro Val Asn Val Gly Tyr Ser Tyr
225                 230                 235                 240

Ser Asn Ser Ala Val Ser Asp Thr Val Ala Ala Gly Lys Asp Val Tyr
                245                 250                 255

Ala Leu Leu Thr Leu Phe Phe Lys Gln Phe Pro Glu Tyr Ala Lys Gln
                260                 265                 270

Asp Phe His Ile Ala Gly Glu Ser Tyr Ala Gly His Tyr Ile Pro Val
            275                 280                 285

Phe Ala Ser Glu Ile Leu Ser His Lys Lys Arg Asn Ile Asn Leu Gln
290                 295                 300

Ser Val Leu Ile Gly Asn Gly Leu Thr Asp Gly Tyr Thr Gln Tyr Glu
305                 310                 315                 320

Tyr Tyr Arg Pro Met Ala Cys Gly Asp Gly Gly Tyr Pro Ala Val Leu
                325                 330                 335

Asp Glu Ser Ser Cys Gln Ser Met Asp Asn Ala Leu Pro Arg Cys Gln
                340                 345                 350

Ser Met Ile Glu Ser Cys Tyr Ser Ser Glu Ser Ala Trp Val Cys Val
            355                 360                 365

Pro Ala Ser Ile Tyr Cys Asn Asn Ala Leu Leu Ala Pro Tyr Gln Arg
370                 375                 380

Thr Gly Gln Asn Val Tyr Asp Val Arg Gly Lys Cys Glu Asp Ser Ser
385                 390                 395                 400

Asn Leu Cys Tyr Ser Ala Met Gly Tyr Val Ser Asp Tyr Leu Asn Lys
                405                 410                 415

Pro Glu Val Ile Glu Ala Val Gly Ala Glu Val Asn Gly Tyr Asp Ser
                420                 425                 430

Cys Asn Phe Asp Ile Asn Arg Asn Phe Leu Phe His Gly Asp Trp Met
            435                 440                 445

Lys Pro Tyr His Arg Leu Val Pro Gly Leu Leu Glu Gln Ile Pro Val
450                 455                 460

Leu Ile Tyr Ala Gly Asp Ala Asp Phe Ile Cys Asn Trp Leu Gly Asn
465                 470                 475                 480

Lys Ala Trp Thr Glu Ala Leu Glu Trp Pro Gly Gln Ala Glu Tyr Ala
                485                 490                 495

Ser Ala Glu Leu Glu Asp Leu Val Ile Val Asp Asn Glu His Thr Gly
                500                 505                 510

Lys Lys Ile Gly Gln Val Lys Ser His Gly Asn Phe Thr Phe Met Arg
            515                 520                 525

Leu Tyr Gly Gly Gly His Met Val Pro Met Asp Gln Pro Glu Ser Ser
530                 535                 540

Leu Glu Phe Phe Asn Arg Trp Leu Gly Gly Glu Trp Phe
545                 550                 555

(2) INFORMATION FOR SEQ ID NO: 3:

(i) SEQUENCE CHARACTERISTICS:
        (A) LENGTH: 2002 base pairs
        (B) TYPE: nucleic acid
        (C) STRANDEDNESS: double
        (D) TOPOLOGY: linear (ii) MOLECULE TYPE: cDNA
```

-continued (vi) ORIGINAL SOURCE:
    (A) ORGANISM: Aspergillus niger (ix) FEATURE:
    (A) NAME/KEY: intron
    (B) LOCATION: 349..411

(ix) FEATURE:
    (A) NAME/KEY: CDS
    (B) LOCATION: join (348..412)

(xi) SEQUENCE DESCRIPTION: SEQ ID NO: 3:

```
GCGGCCGCTG CTACTTGCTT TTTCTAATTT GATACTTTTG TGTCCGTACC GTACCTTCCA          60

GACCGCAAGG TACCCATCCT CTACCTACTC ATCCCATCAT CATCTCGATT TCATACCAAC         120

CCCGTTGGGT TTCAACACA ATG AGA GTT CTT CCA GCT GCT ATG CTG GTT GGA          172
                     Met Arg Val Leu Pro Ala Ala Met Leu Val Gly
                       1               5                      10

GCG GGC ACT GCG GCC GTC CCT CCC TTC CAG CAG GTC CTT GGA GGT AAC           220
Ala Gly Thr Ala Ala Val Pro Pro Phe Gln Gln Val Leu Gly Gly Asn
             15                  20                  25

GGT GCC AAG CAC GGT GCC GAC CAT GCG GCC GAG GTC CCT GCG GAT CAC           268
Gly Ala Lys His Gly Ala Asp His Ala Ala Glu Val Pro Ala Asp His
         30                  35                  40

AGT GCC GAC GGG TTC TCC AAG CCG CTG CAC GCA TTC CAG GAG GAG CTG           316
Ser Ala Asp Gly Phe Ser Lys Pro Leu His Ala Phe Gln Glu Glu Leu
     45                  50                  55

AAG TCT CTC TCT GAT GAG GCT CGT AAG CTC TGG GAT GAG GTT GCT AGC           364
Lys Ser Leu Ser Asp Glu Ala Arg Lys Leu Trp Asp Glu Val Ala Ser
 60                  65                  70                  75

TTC TTC CCG GAG AGC ATG GAT CAG AAC CCT CTC TTC TCC CTC CCC AAG           412
Phe Phe Pro Glu Ser Met Asp Gln Asn Pro Leu Phe Ser Leu Pro Lys
                 80                  85                  90

AAG CAC AAC CGC CGC CCC GAC CAC CAC TGG GAC CAC ATC GTC CGC GGC           460
Lys His Asn Arg Arg Pro Asp His His Trp Asp His Ile Val Arg Gly
             95                 100                 105

TCC GAC GTT CAG AGC GTC TGG GTT ACT GGT GAG AAC GGT GAG AAG GAG           508
Ser Asp Val Gln Ser Val Trp Val Thr Gly Glu Asn Gly Glu Lys Glu
        110                 115                 120

CGT GAG GTC GAT GGC AAG CTG GAA GCC TAT GAT CTC AGG GTC AAG AAG           556
Arg Glu Val Asp Gly Lys Leu Glu Ala Tyr Asp Leu Arg Val Lys Lys
    125                 130                 135

ACC GAT CCT AGC TCT CTT GGC ATC GAC CCT GGC GTA AAG CAG TAC ACC           604
Thr Asp Pro Ser Ser Leu Gly Ile Asp Pro Gly Val Lys Gln Tyr Thr
140                 145                 150                 155

GGT TAT CTC GAT GAC AAC GAG AAC GAC AAG CAT CTG TTC TAC TGG TTC           652
Gly Tyr Leu Asp Asp Asn Glu Asn Asp Lys His Leu Phe Tyr Trp Phe
                160                 165                 170

TTC GAG TCT CGC AAT GAC CCC GAG AAT GAC CCT GTT GTT CTG TGG CTG           700
Phe Glu Ser Arg Asn Asp Pro Glu Asn Asp Pro Val Val Leu Trp Leu
            175                 180                 185

AAC GGT GGC CCT GGA TGC TCT TCC CTC ACC GGT CTT TTC ATG GAG CTC           748
Asn Gly Gly Pro Gly Cys Ser Ser Leu Thr Gly Leu Phe Met Glu Leu
        190                 195                 200

GGC CCT AGC AGC ATC AAC AAG AAG ATC CAG CCG GTC TAC AAC GAC TAC           796
Gly Pro Ser Ser Ile Asn Lys Lys Ile Gln Pro Val Tyr Asn Asp Tyr
    205                 210                 215

GCT TGG AAC TCC AAC GCG TCC GTG ATC TTC CTT GAC CAG CCT GTC AAC           844
Ala Trp Asn Ser Asn Ala Ser Val Ile Phe Leu Asp Gln Pro Val Asn
220                 225                 230                 235

GTC GGT TAC TCT TAC AGC AAC TCT GCT GTC AGC GAC ACC GTT GCT GCT           892
Val Gly Tyr Ser Tyr Ser Asn Ser Ala Val Ser Asp Thr Val Ala Ala
                240                 245                 250
```

```
GGC AAG GAC GTC TAT GCC TTG CTT ACC CTC TTC TTC AAA CAA TTC CCC        940
Gly Lys Asp Val Tyr Ala Leu Leu Thr Leu Phe Phe Lys Gln Phe Pro
            255                 260                 265

GAG TAT GCC AAG CAG GAC TTC CAC ATT GCC GGT GAA TCC TAT GCT GGT        988
Glu Tyr Ala Lys Gln Asp Phe His Ile Ala Gly Glu Ser Tyr Ala Gly
        270                 275                 280

CAC TAT ATC CCC GTC TTT GCT TCG GAG ATT TTG TCT CAC AAG AAG CGC       1036
His Tyr Ile Pro Val Phe Ala Ser Glu Ile Leu Ser His Lys Lys Arg
285                 290                 295

AAC ATC AAC CTG CAG TCC GTT CTT ATT GGC AAC GGT CTC ACC GAC GGT       1084
Asn Ile Asn Leu Gln Ser Val Leu Ile Gly Asn Gly Leu Thr Asp Gly
300                 305                 310                 315

CTC ACT CAG TAC GAG TAC TAC CGT CCC ATG GCC TGT GGT GAC GGT GGT       1132
Leu Thr Gln Tyr Glu Tyr Tyr Arg Pro Met Ala Cys Gly Asp Gly Gly
            320                 325                 330

TAC CCA GCT GTC TTG GAC GAG GGC TCC TGC CAG GCC ATG GAC AAC GCC       1180
Tyr Pro Ala Val Leu Asp Glu Gly Ser Cys Gln Ala Met Asp Asn Ala
                335                 340                 345

CTT CCT CGC TGC CAG TCT ATG ATT GAG TCT TGC TAT AGT TCC GAG AGC       1228
Leu Pro Arg Cys Gln Ser Met Ile Glu Ser Cys Tyr Ser Ser Glu Ser
        350                 355                 360

GCT TGG GTT TGT GTC CCG GCC TCC ATC TAC TGT AAC AAC GCC CTC CTT       1276
Ala Trp Val Cys Val Pro Ala Ser Ile Tyr Cys Asn Asn Ala Leu Leu
365                 370                 375

GCC CCT TAC CAG CGC ACC GGA CAG AAC GTC TAC GAT GTT CGT GGT AAG       1324
Ala Pro Tyr Gln Arg Thr Gly Gln Asn Val Tyr Asp Val Arg Gly Lys
380                 385                 390                 395

TGC GAG GAT AGC TCC AAC CTC TGC TAC TCG GCC ATG GGC TAC GTC AGC       1372
Cys Glu Asp Ser Ser Asn Leu Cys Tyr Ser Ala Met Gly Tyr Val Ser
            400                 405                 410

GAC TAC CTG AAC AAG ACC GAG GTC ATT GAG GCT GTT GGC GCT GAG GTC       1420
Asp Tyr Leu Asn Lys Thr Glu Val Ile Glu Ala Val Gly Ala Glu Val
                415                 420                 425

AAC GGC TAC GAC TCG TGC AAC TTT GAC ATC AAC CGC AAC TTC CTC TTC       1468
Asn Gly Tyr Asp Ser Cys Asn Phe Asp Ile Asn Arg Asn Phe Leu Phe
        430                 435                 440

CAC GGT GAC TGG ATG AAG CCC TAC CAC CGT CTC GTT CCG GGA CTC CTG       1516
His Gly Asp Trp Met Lys Pro Tyr His Arg Leu Val Pro Gly Leu Leu
445                 450                 455

GAG CAG ATC CCT GTC CTG ATC TAC GCT GGT GAC GCC GAT TTC ATC TGC       1564
Glu Gln Ile Pro Val Leu Ile Tyr Ala Gly Asp Ala Asp Phe Ile Cys
460                 465                 470                 475

AAC TGG CTG GGC AAC AAG GCC TGG ACT GAA GCC CTT GAG TGG CCC GGA       1612
Asn Trp Leu Gly Asn Lys Ala Trp Thr Glu Ala Leu Glu Trp Pro Gly
            480                 485                 490

CAG GCT GAA TAT GCC TCC GCT AAG CTG GAG GAC CTG GTC GTG GTC GAG       1660
Gln Ala Glu Tyr Ala Ser Ala Lys Leu Glu Asp Leu Val Val Val Glu
                495                 500                 505

AAT GAG CAC AAG GGC AAG AAG ATC GGC CAG GTC AAG TCC CAT GGC AAC       1708
Asn Glu His Lys Gly Lys Lys Ile Gly Gln Val Lys Ser His Gly Asn
        510                 515                 520

TTC ACC TTC ATG CGT CTC TAT GGC GGT GGC CAC ATG GTC CCG ATG GAC       1756
Phe Thr Phe Met Arg Leu Tyr Gly Gly Gly His Met Val Pro Met Asp
525                 530                 535

CAA CCC GAG TCG AGT CTT GAA TTC TTC AAC CGC TGG TTG GGA GGT GAA       1804
Gln Pro Glu Ser Ser Leu Glu Phe Phe Asn Arg Trp Leu Gly Gly Glu
540                 545                 550                 555
```

```
TGG TTT TAA AGACGTGCTA TCACCGCATA TAGACTTTCC GGTCATTTCG GTGACACTGC  1863
Trp Phe

AGATATGTTT CTTAACGATA GTTTGAGGAT GCTTGTCAAT GCCCACTAAT CCCGAGCCTT  1923

ATGTTACATG GTATCTATGA GTTTGTCATT ATAGTGCATT ATGCATTTGT ACTCCGTACG  1983

AGAATGAATC AGCGGCCGC                                                2002
```

(2) INFORMATION FOR SEQ ID NO: 4:

(i) SEQUENCE CHARACTERISTICS:
        (A) LENGTH: 557 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Aspergillus Niger (xi) SEQUENCE DESCRIPTION: SEQ ID NO: 4:

```
Met Arg Val Leu Pro Ala Ala Met Leu Val Gly Ala Gly Thr Ala Ala
1               5                   10                  15

Val Pro Pro Phe Gln Gln Val Leu Gly Gly Asn Gly Ala Lys His Gly
                20                  25                  30

Ala Asp His Ala Ala Glu Val Pro Ala Asp His Ser Ala Asp Gly Phe
            35                  40                  45

Ser Lys Pro Leu His Ala Phe Gln Glu Glu Leu Lys Ser Leu Ser Asp
        50                  55                  60

Glu Ala Arg Lys Leu Trp Asp Glu Val Ala Ser Phe Phe Pro Glu Ser
65                  70                  75                  80

Met Asp Gln Asn Pro Leu Phe Ser Leu Pro Lys Lys His Asn Arg Arg
                85                  90                  95

Pro Asp His His Trp Asp His Ile Val Arg Gly Ser Asp Val Gln Ser
            100                 105                 110

Val Trp Val Thr Gly Glu Asn Gly Glu Lys Glu Arg Glu Val Asp Gly
        115                 120                 125

Lys Leu Glu Ala Tyr Asp Leu Arg Val Lys Lys Thr Asp Pro Ser Ser
    130                 135                 140

Leu Gly Ile Asp Pro Gly Val Lys Gln Tyr Thr Gly Tyr Leu Asp Asp
145                 150                 155                 160

Asn Glu Asn Asp Lys His Leu Phe Tyr Trp Phe Phe Glu Ser Arg Asn
                165                 170                 175

Asp Pro Glu Asn Asp Pro Val Val Leu Trp Leu Asn Gly Gly Pro Gly
            180                 185                 190

Cys Ser Ser Leu Thr Gly Leu Phe Met Glu Leu Gly Pro Ser Ser Ile
        195                 200                 205

Asn Lys Lys Ile Gln Pro Val Tyr Asn Asp Tyr Ala Trp Asn Ser Asn
    210                 215                 220

Ala Ser Val Ile Phe Leu Asp Gln Pro Val Asn Val Gly Tyr Ser Tyr
225                 230                 235                 240

Ser Asn Ser Ala Val Ser Asp Thr Val Ala Ala Gly Lys Asp Val Tyr
                245                 250                 255

Ala Leu Leu Thr Leu Phe Phe Lys Gln Phe Pro Glu Tyr Ala Lys Gln
            260                 265                 270

Asp Phe His Ile Ala Gly Glu Ser Tyr Ala Gly His Tyr Ile Pro Val
        275                 280                 285
```

```
                                    -continued

Phe Ala Ser Glu Ile Leu Ser His Lys Lys Arg Asn Ile Asn Leu Gln
    290                 295                 300

Ser Val Leu Ile Gly Asn Gly Leu Thr Asp Gly Leu Thr Gln Tyr Glu
305                 310                 315                 320

Tyr Tyr Arg Pro Met Ala Cys Gly Asp Gly Tyr Pro Ala Val Leu
                325                 330                 335

Asp Glu Gly Ser Cys Gln Ala Met Asp Asn Ala Leu Pro Arg Cys Gln
            340                 345                 350

Ser Met Ile Glu Ser Cys Tyr Ser Ser Glu Ser Ala Trp Val Cys Val
        355                 360                 365

Pro Ala Ser Ile Tyr Cys Asn Asn Ala Leu Leu Ala Pro Tyr Gln Arg
    370                 375                 380

Thr Gly Gln Asn Val Tyr Asp Val Arg Gly Lys Cys Glu Asp Ser Ser
385                 390                 395                 400

Asn Leu Cys Tyr Ser Ala Met Gly Tyr Val Ser Asp Tyr Leu Asn Lys
                405                 410                 415

Thr Glu Val Ile Glu Ala Val Gly Ala Glu Val Asn Gly Tyr Asp Ser
            420                 425                 430

Cys Asn Phe Asp Ile Asn Arg Asn Phe Leu Phe His Gly Asp Trp Met
        435                 440                 445

Lys Pro Tyr His Arg Leu Val Pro Gly Leu Leu Glu Gln Ile Pro Val
    450                 455                 460

Leu Ile Tyr Ala Gly Asp Ala Asp Phe Ile Cys Asn Trp Leu Gly Asn
465                 470                 475                 480

Lys Ala Trp Thr Glu Ala Leu Glu Trp Pro Gly Gln Ala Glu Tyr Ala
                485                 490                 495

Ser Ala Lys Leu Glu Asp Leu Val Val Glu Asn Glu His Lys Gly
            500                 505                 510

Lys Lys Ile Gly Gln Val Lys Ser His Gly Asn Phe Thr Phe Met Arg
        515                 520                 525

Leu Tyr Gly Gly His Met Val Pro Met Asp Gln Pro Glu Ser Ser
    530                 535                 540

Leu Glu Phe Phe Asn Arg Trp Leu Gly Gly Glu Trp Phe
545                 550                 555
```